(12) United States Patent
Misicka-Kesik et al.

(10) Patent No.: US 10,800,814 B2
(45) Date of Patent: Oct. 13, 2020

(54) CYCLIC PEPTIDOMIMETICS, COMPOSITIONS CONTAINING THEM AND THEIR USE IN THE TREATMENT OF DISEASES ASSOCIATED WITH ANGIOGENESIS

(71) Applicant: UNIWERSYTET WARSZAWSKI, Warsaw (PL)

(72) Inventors: Aleksandra Misicka-Kesik, Piastow (PL); Karolina Grabowska, Warsaw (PL); Anna Puszko, Warsaw (PL); Anna Niescioruk, Biala Podlaska (PL); Piotr Sosnowski, Czerwin (PL); Bartlomiej Fedorczyk, Warsaw (PL); Dagmara Tymecka, Warsaw (PL); Beata Wilenska, Piastow (PL); Ewa Witkowska, Zielonka (PL)

(73) Assignee: UNIWERSYTET WARSZAWSKI, Warsaw (PL)

(*) Notice: Subject to any disclaimer, the term of this patent is extended or adjusted under 35 U.S.C. 154(b) by 9 days.

(21) Appl. No.: 15/755,792

(22) PCT Filed: Aug. 29, 2016

(86) PCT No.: PCT/IB2016/001247
§ 371 (c)(1),
(2) Date: Feb. 27, 2018

(87) PCT Pub. No.: WO2017/033055
PCT Pub. Date: Mar. 2, 2017

(65) Prior Publication Data
US 2018/0327455 A1 Nov. 15, 2018

(30) Foreign Application Priority Data
Aug. 27, 2015 (PL) .......................... 413705

(51) Int. Cl.
| | | |
|---|---|---|
| *C07K 7/56* | (2006.01) | |
| *C07K 5/11* | (2006.01) | |
| *C07K 5/02* | (2006.01) | |
| *A61P 7/00* | (2006.01) | |
| *A61P 37/06* | (2006.01) | |
| *A61P 35/00* | (2006.01) | |
| *A61K 38/00* | (2006.01) | |
| *A61K 9/00* | (2006.01) | |
| *A61K 38/12* | (2006.01) | |

(52) U.S. Cl.
CPC .......... *C07K 7/56* (2013.01); *A61P 7/00* (2018.01); *A61P 35/00* (2018.01); *A61P 37/06* (2018.01); *C07K 5/0215* (2013.01); *C07K 5/1019* (2013.01); *A61K 9/0019* (2013.01); *A61K 38/00* (2013.01); *A61K 38/12* (2013.01)

(58) Field of Classification Search
None
See application file for complete search history.

(56) References Cited

FOREIGN PATENT DOCUMENTS

WO WO 2015/026251 * 2/2015

OTHER PUBLICATIONS

Grabowska et al. ('Design, synthesis and in vitro biological evaluation of a small cyclic peptide as inhibitor of vascular endothelial growth factor binding to neuropilin-1' Bioorganic & Medicinal Chemistry Letters v26 2016 pp. 2843-2846) (Year: 2016).*
Dixon et al. ('Nomenclature and symbolism for amino acids and peptides' Biochem J v219 1984 pp. 345-373) (Year: 1984).*
Grabowskasupplement (Supplementary Material for 'Design, synthesis and in vitro biological evaluation of a small cyclic peptide as inhibitor of vascular endothelial growth factor binding to neuropilin-1' Bioorganic & Medicinal Chemistry Letters v26 2016 5 pages) (Year: 2016).*

* cited by examiner

*Primary Examiner* — Ronald T Niebauer
(74) *Attorney, Agent, or Firm* — Browdy and Neimark, PLLC

(57) ABSTRACT

The present invention relates to novel cyclic peptidomimetics, pharmaceutical compositions containing them and their use in the treatment of diseases associated with angiogenesis especially tumors and chronic inflammation in psoriasis, diabetes, degenerative diseases of the eye (ARMD), nephropathy and neuropathy.

13 Claims, 1 Drawing Sheet
Specification includes a Sequence Listing.

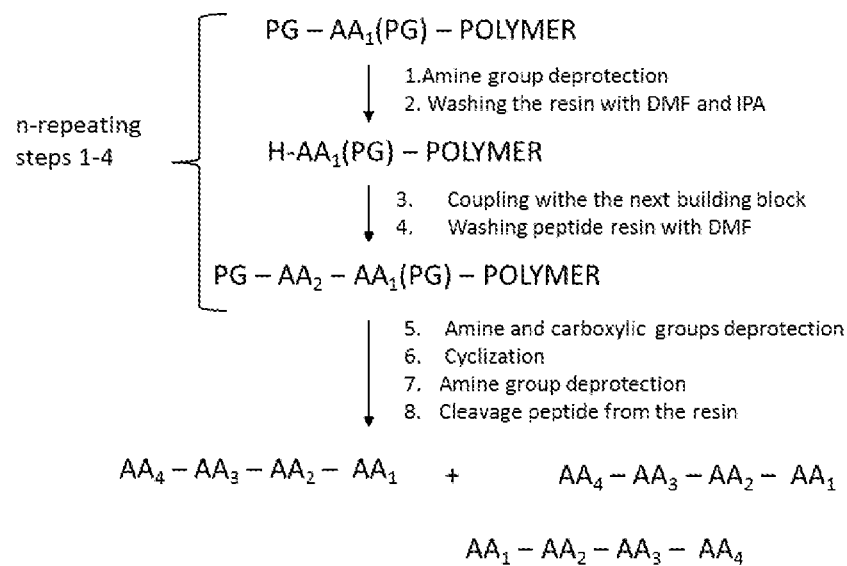

CYCLIC PEPTIDOMIMETICS, COMPOSITIONS CONTAINING THEM AND THEIR USE IN THE TREATMENT OF DISEASES ASSOCIATED WITH ANGIOGENESIS

The Sequence Listing in ASCII text file format of 815 bytes in size, created on Nov. 18, 2019, with the file name "2019-11-18SequenceListing_MISICKA1," filed in the U.S. Patent and Trademark Office on even date herewith, is hereby incorporated herein by reference.

The subject of the present invention are novel cyclic peptidomimetics, their pharmaceutical compositions and their use in the treatment of angiogenesis, particularly in cancer, chronic inflammation in psoriasis, diabetes, age-related macular degeneration (ARMD), nephropathy and neuropathy.

Angiogenesis is a biological process in which new blood vessels are created from pre-existing ones in the body by vascular endothelial cells. There are two types of angiogenesis: physiological and pathological. Excessive angiogenesis occurs for instance at sites of inflammation. The intensiveness of angiogenesis related diseases or neoplasms is so high, that it becomes pathological. Such high angiogenesis is observed in many types of diseases, e.g. endometriosis, psoriasis, peptic ulcer disease and rheumatoid arthritis. During the formation of neoplasms, angiogenesis is necessary for the growth of tumors beyond 2-3 mm, as well as for metastases.

One of the most important proteins, which contribute to angiogenesis are Vascular Endothelial Growth Factors (VEGF). The strongest proangiogenic effect is induced by $VEGF_{165}$, which binds to its receptors and signals endothelial cells to proliferate. The most important $VEGF_{165}$ receptor is VEGF Receptor 2 (VEGFR2), a tyrosine kinase, which in the presence of a co-receptor—cell surface protein called neuropilin-1 (NRP-1) interacts with $VEGF_{165}$. This evokes a strong proangiogenic signal, therefore molecules, which are able to block the formation of the $VEGF_{165}$/VEGFR2/NRP-1 complex could become prospective anti-tumor drugs.

In publications: Cook, K M, and Figg, W D "*Angiogenesis inhibitors: current strategies and future prospects*" Cancer J. Clin. 60, 222, 2010 and Folkman, J. "*Tumor angiogenesis; therapeutic implications*". N. Engl. J. Med. 285, 1182, 1976 mechanism of development of angiogenesis including VEGF receptor was described. Publication of Samant, R S and Whevde, L A "*Recent advances in anti-angiogenic therapy of cancer*" Oncotarget 2, 122, 2011 describes the latest research on tumor growth, metathesis, treatment of angiogenesis using individual agents or combination with other chemotherapeutic agents.

So far, there are linear peptides known to exhibit antiangiogenic properties. Notification WO 2015/026251 reveals peptidomimetics with antiangiogenic activity and compositions comprising them.

There are also known cyclic peptides with antiangiogenic properties. For example American Patent U.S. Pat. No. 2,690,107 reveals cyclic peptides with anticancer and antiangiogenic properties. The document specifies amino acids sequences and their conjugates. This document also discloses application of cyclic peptides according to invention for drug preparation and treatment of cancer or for the treatment of adverse conditions associated with cell proliferation or blood vessels development or method of treatment mentioned above with using a pharmaceutical composition comprising an effective amount of at least one of the disclosed cyclic peptides.

Document US 20070178045 reveals cyclic peptides and their pharmaceutical composition, which contains at least one of the claimed compounds in a mixture with a base or an acceptable pharmaceutical addition. The document also claims application of the compounds to the drug preparation and treatment with the use of such drugs in diseases stemming from abnormal angiogenesis, tumors, eye diseases, and rheumatoid arthritis. Document WO 2006092722 reveals cyclic peptides and the preparation of these compounds for the manufacture of medicaments affecting angiogenesis or for treatment and prevention of cancer diseases.

In many cases, not all previously known compounds, which have shown antiangiogenic potential receive good results in clinical tests and get marketed as drug components. The main obstacle is toxicity of such compounds.

During the last 20 years big pharmaceutical companies focused their efforts on the production of new drugs, in which the active compounds were small molecules. Such molecules had a potential to be used as an oral medication. Unfortunately, these compounds mostly exhibit relatively high toxicity.

Until now, there are only few drugs with an antiangiogenic and anticancer properties on the market. These medicines are acting on VEGF (e.g. AVASTIN, bevacizumab, a humanized monoclonal antibody targeting vascular endothelial growth factor A (VEGF-A)) or VEGFR receptors (eg. Sorafenib). There are still no drugs, which would directly inhibit VEGF/NRP-1 complex. A lot of new research shows, that this interaction is responsible for the pathological angiogenesis. Recent years indicated that NRP-1 is present in the membranes of tumor cells in elevated concentrations. Therefore, this protein is assumed to be $VEGF_{165}$ receptor, that mediates the transfer of the signal and produces proangiogenic tumor progression.

Accordingly, there is a need for developing novel compounds, that are inhibitors of $VEGF_{165}$/NRP-1. They might become prospective antiangiogenic and anticancer drugs and can be used in anticancer targeted therapy.

Peptides in general are poor candidates to use as drugs, because of their fast enzymatic degradation in physiological fluids. Cyclic peptides are a favorable alternative due to their lower susceptibility to both exopeptidases and endopeptidases. This results in their greater stability. Many natural peptides (e.g., oxytocin, vasopressin, somatostatin, and gramicidin) and many peptide drugs (Octreotide, Ziconotide) are cyclic.

The aim of the invention is to produce novel cyclic peptides having the desired activity and preferred characteristics with respect to their stability.

The invention disclosed in this document is a response to the needs of the medical sector related to tumors, chronic inflammation (rheumatoid arthritis, inflammatory bowel disease), psoriasis, diabetes, degenerative diseases of the eye (ARMD), nephropathy and neuropathy.

The present invention relates to cyclic peptidomimetics of the general formula I:

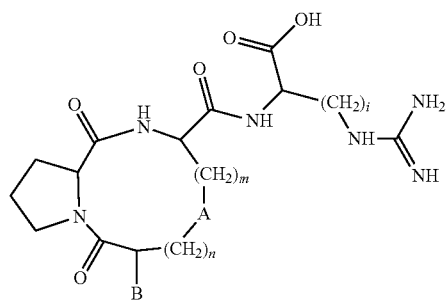

where m=from 0 to 4, n=from 0 to 4, i=3 or 4, and where A is selected from the group: —CO—NH—; —NH—CO—; —S—S—; —HN—CO—NH—, $CH_2$—$CH_2$—; —$CH_2$—NH—; —NH—$CH_2$—;

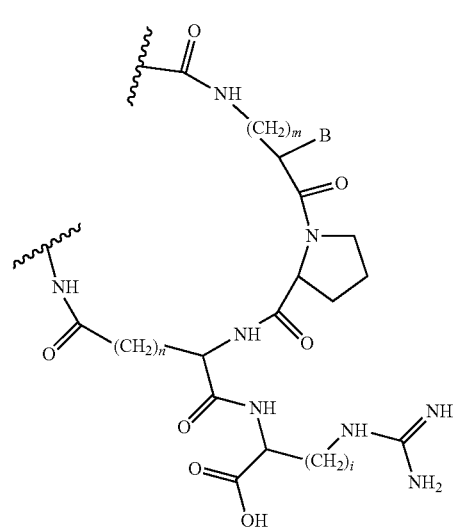

B is selected from the group: —$(CH_2)_d$—$NH_2$, where d=from 0 to 4;

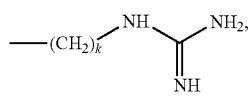

where k=3 or 4,
wherein at each chiral center may be L or D configuration or the R or S, and pharmaceutically acceptable salts, hydrates or other pharmaceutically acceptable complexes.

Preferably, the cyclic peptidomimetics exhibit an inhibiting binding of $VEGF_{165}$/NRP-1.

Preferably, the cyclic peptidomimetics exhibit antiangiogenic properties.

Preferably, the cyclic peptidomimetics are monomers of the general formula:

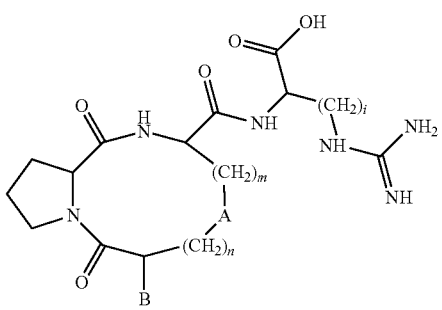

where m=from 0 to 4, n=from 0 to 4, i=3 or 4, and where A is selected from the group: —CO—NH—; —NH—CO—; —S—S—; —HN—CO—NH—, $CH_2$—$CH_2$—; —$CH_2$—NH—; —NH—$CH_2$—,

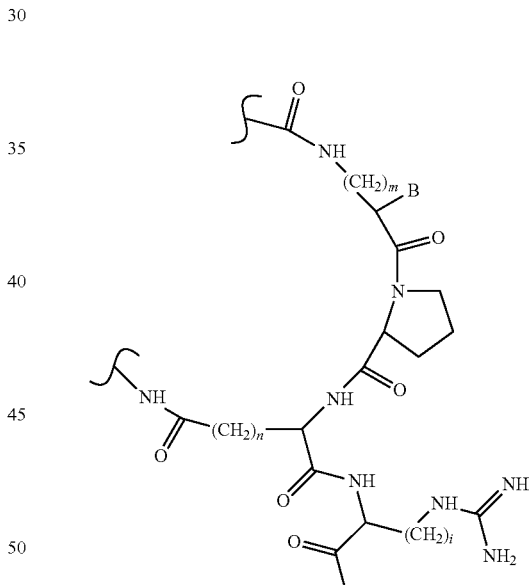

B is selected from the group: —$(CH_2)_d$—$NH_2$, where d=from 0 to 4;

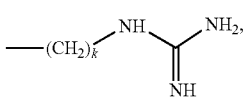

where k=3 or 4,
wherein at each chiral center may be L or D configuration or the R or S, and pharmaceutically acceptable salts, hydrates or other pharmaceutically acceptable complexes.

Also preferably, the cyclic peptidomimetics are dimers of the general formula:

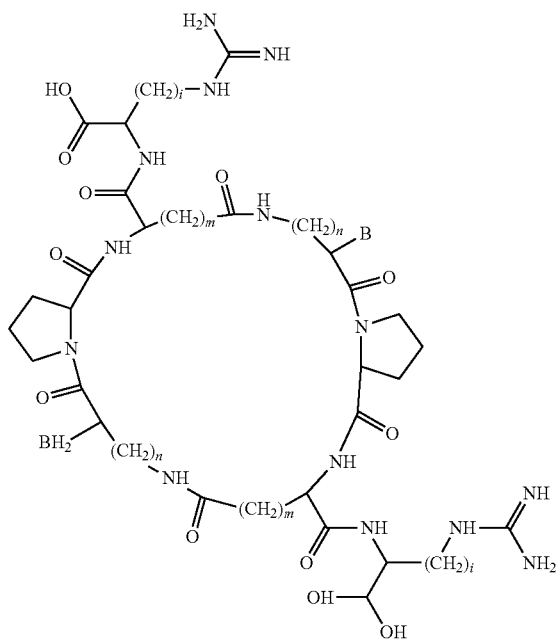

where m=from 0 to 4, n=from 0 to 4, i=3 or 4, and B is selected from the group: —(CH$_2$)$_d$—NH$_2$, where d=from 0 to 4;

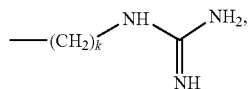

where k=3 or 4, wherein at each chiral center may be L or D configuration or the R or S, and pharmaceutically acceptable salts, hydrates or other pharmaceutically acceptable complexes.

Preferably, the cyclic peptidomimetics are compounds of the general formula:
(c[Lys-Pro-Glu]-Arg-OH)$_2$
(c[Dab-Pro-Glu]-Arg-OH)$_2$
(H-c[Dab-Pro-Glu]-Arg-OH)$_2$
(c[Arg-Pro-Glu]-Arg-OH)$_2$
H-c[Lys-Pro-Glu]-Arg-OH
where c means cyclic.

Another object of the invention is a pharmaceutical composition for the treatment of diseases associated with angiogenesis, comprising an active substance and a pharmaceutically acceptable carrier and/or pharmaceutically acceptable additives, in which as active ingredient is a cyclic peptidomimetics as defined above.

Preferably, when the composition is for treating cancer and/or chronic inflammation, psoriasis, diabetes, degenerative diseases of the eye (ARMD), nephropathy and neuropathy.

Another object of the invention is the use of a compound, as defined in claim as above, for the manufacture of a medicament for the treatment of diseases associated with angiogenesis.

Preferably, the diseases are tumors, chronic inflammation, psoriasis, diabetes, degenerative eye diseases (ARMD), nephropathy and neuropathy.

Preferably, chronic inflammation and rheumatoid arthritis, inflammatory bowel disease.

Preferably, the medicament is adapted in a dosage form for infusion or intravenous injections or implants.

The advantage of cyclic peptidomimetics, which are subjects of the invention is their antiangiogenic activity in a large range of concentration, as it will be shown in the embodiments of the invention. Due to their cyclic structure they are more stable in body fluids (preliminary studies show t ½ approx. 6 hrs.) and their degradation leads to the amino acids, that are not toxic.

BRIEF DESCRIPTION OF THE DRAWING

FIG. 1 shows the general scheme of the synthesis of peptidomimetics of the invention.

The Synthesis of the Compounds of the Invention

The cyclic peptidomimetics of the invention may be obtained using well known peptide synthesis on the polymeric support (Solid Phase Peptide Synthesis, SPPS), where the building block's functional groups are protected by orthogonal protective groups cleavable in acidic or basic conditions.

All used protecting groups should be stable during peptide bond or its isostere synthesis, while their removal should not lead to the destruction of the growing peptide chain or racemization of any chiral center.

The preferred N-α-protecting groups are: 9-fluorenylmethyloxycarbonyl group (Fmoc) or tert-butyloxycarbonyl group (Boc). Other protecting groups proposed for the protection of chemical moieties located in the side chains of building blocks are: 2,2,4,6,7-pentamethyl-dihydrobenzofurane-5-sulfonyl group (Pbf), 2,2,5,7,8-pentamethylchromane-6-sulfonyl group (Pmc), 4-methoxy-2,3,6-trimethylbenzylsulfonyl group (Mtr), p-toluenesulfonyl group (Tos), Boc, Fmoc, 4-methyltrityl group (Mtt), 4-methoxytrityl group (Mmt), benzyloxycarbonyl group (Cbz, Z), 1-(4,4-Dimethyl-2,6-dioxocyclohex-1-ylidene)-3-methyl-butyl group (ivDde), 2-chlorobenzyloxycarbonyl group (2-Cl-Z). For the synthesis of all cyclic peptidomimetics C-terminal amino acids are attached to a polymeric support, which is chemically inert and insoluble in the reaction media used. The preferred resin for the peptide synthesis in the Fmoc strategy is the 4-(hydroxymethyl)phenoxymethyl linker, which is directly attached to a polystyrene base matrix (Wang resin). The chloromethylpolystyrene with 1% of divinylbenzene (Merrifeild resin) and 4-Hydroxymethylphenylacetamidomethyl (PAM resin) are preferred resins for the peptide synthesis in the Boc strategy.

Peptide bonds were obtained by using the following coupling reagents: N,N'-Dicyclohexylcarbodiimide (DCC) with addition of 1-Hydroxybenzotriazole (HOBt), N,N'-Diisopropylcarbodiimide (DIC) with addition of 1-Hydroxybenzotriazole (HOBt), N,N'-dicyclohexylcarbodiimide with addition of hydroxybenzotriazole (HOBt), N,N'-diisopropylcarbodiimide with addition of HOBt, N,N,N',N'-tetramethyl-O-(1H-benzotriazol-1-yl)uranium hexafluorophosphate (HBTU), N,N,N',N'-tetramethyl-O-(benzotriazol-1-yl)uronium tetrafluoroborate (TBTU), 1-[bis(dimethylamino)methylene]-1H-1,2,3-triazolo[4,5-b]pyridinium 3-oxid hexafluorophosphate (HATU), (1-cyano-2-ethoxy-2-oxo-ethylidenaminooxy)dimethyl-amino-morpholino-carbenium hexafluorophosphate (COMU), benzotriazol-1-yloxy-tris(dimethylamino)phosphonium hexafluorophosphate (BOP).

After deprotection of carboxylic group and amine group located in the side chains of amino acids in the position 2 and 4 cyclization on the resin was carried out using uronium salt (TBTU, HATU).

The final step during the synthesis was peptide cleavage from the solid support. This process depends on the used strategy during peptide synthesis. The preferred is to use liquid hydrogen fluoride (HF) with the addition of anisole or a mixture of trifluoroacetic acid/water/triisopropylsilane (95:2.5:2.5; v/v/v). The crude products may be purified using high performance liquid chromatography on a reverse phase column packed with a C-12 or C-18 with the use of gradient method 0%-30% (B) over 30 minutes, where phase (A) is 0.05% TFA in H$_2$O and the phase (B) is 0.05% TFA in ACN.

The obtained products can be converted into a desired pharmaceutically acceptable salt by a conventional method.

EXAMPLE 1

The Synthesis of the Compound of the Formula 1 wherein A:

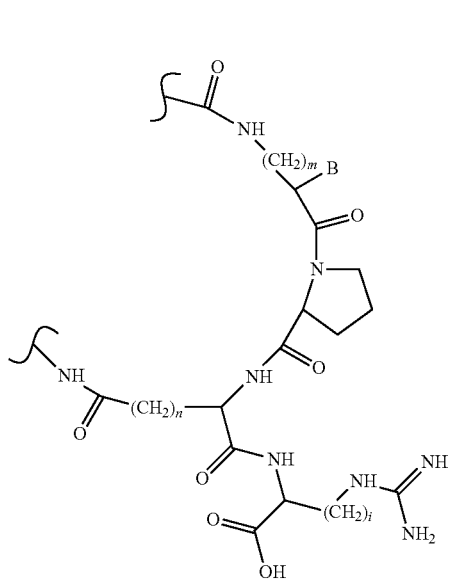

B=—(CH$_2$)$_4$—NH$_2$, m=2, n=4; compound (c[Lys-Pro-Glu]-Arg-OH)$_2$

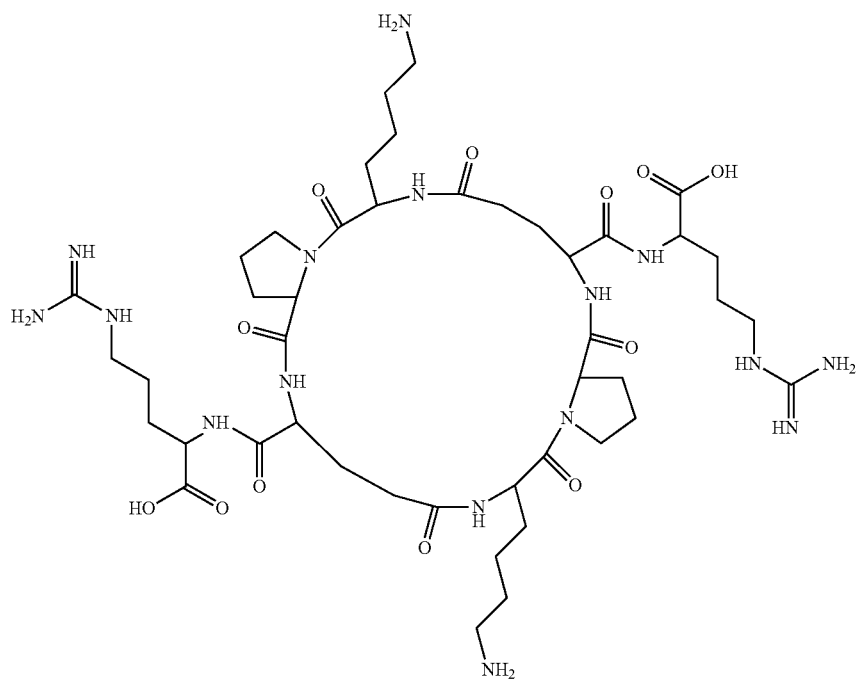 [SMILES: N=C(N)NCCCC(NC(=O)C1CCC(=O)NC(CCCCN)C(=O)N2CCCC2C(=O)NC(C(=O)NC(CCCNC(=N)N)C(=O)O)CCC(=O)NC(CCCCN)C(=O)N2CCCC2C(=O)N1)C(=O)O]

333 mg (0.2 mmol/g) Boc-Arg-PAM resin with loading 0.37 mmol/g was stirred in methylene chloride (DCM). Boc protecting group was deprotected by 55% TFA in DCM (2×, 5 i 25 min.). After that resin was washed by DCM (3×), 5% DIPEA in DCM (2×), DCM (3×), IPA (3×), DCM (3×). The next step was a Kaiser test procedure. For this purpose to test tube were added dropwise equal volumes (a few drops) of three solutions [(A): 5 g of ninhidrine in 100 ml of ethanol; (B): 80 g of phenol in 20 ml of ethanol; (C): 2 ml 0.001M aqueous KCN in 98 ml of pyridine], then small amount of resin beads was added and after that sample was warmed to 100° C. and left for 5 minutes. When positive result was achieved (navy blue color) the next step of synthesis was carried out. Coupling of the next amino acid Fmoc-Glu(t-Bu)—OH 249 mg (0.6 mmol) was carried out in DMF using 187 mg (0.6 mmol) TBTU and 271 µl (1.2 mmol) DIPEA (2 h). After that time, the resin was washed with DMF (3×) and the Kaiser test was performed—it was negative. The Fmoc protecting group was removed by 20% piperidine in DMF (5 and 20 min). Next, the resin was washed with DMF (3×), IPA (3×), DMF (3×). The Kaiser test was positive. Further, amino acid in a sequence Fmoc-Pro-OH 187 mg (0.6 mmol) was coupled in DMF (2 h) with TBTU and 271 µl (1.2 mmol) DIPEA. The result of Kaiser test was negative. The Fmoc protecting group was removed by 20% piperidine in DMF (5 and 20 min). After that, the resin was washed with DMF (3×), IPA (3×), DMF (3×). This step of the synthesis was followed by the chloranil test. For this purpose a few resin beads were placed in small test tube and few drops (equal volumes) of the two solutions [(A): 2% acetaldehyde in DMF; (B): 2% chloranil in DMF] were added. After short mixing the mixture was left at room temperature for 5 minutes. Subsequently, the dark green color of beads of resin indicated the completion of the Fmoc cleavage from Proline residue. Next, amino acid Boc-Lys(Fmoc)-OH, 274 mg (0.6 mmol) was coupled in DMF (2 h) with 187 mg (0.6 mmol) TBTU and 271 µl (1.2 mmol) DIPEA. The result of the obtained chloranil test was negative. Next, the t-Bu protecting group from carboxylic group from glutamic acid and Boc protecting group from alfa-amine group from lysine was removed. For this purpose the peptide resin was washed with DCM (2×) and 55% TFA in DCM (2×) was added to the resin. Next, the resin was washed with DCM (3×), 5% DIPEA w DCM (2×), DCM (3×), IPA (3×), DCM (3×). The Kaiser test was positive. After that, the amide bond was synthesized to obtain cyclic product. Here we use 187 mg TBTU (0.6 mmol), 102 mg 6-Cl-HOBt (0.6 mmol) i 271 µl DIPEA (1.2 mmol). The reaction was performed in DMF for 4 h. After washing the resin with DMF (3×) the Kaiser test was proceeded—it was positive. Another portion of the reagents were weighed and the reaction was continued for 12 h. After this time, the resin was washed with DMF (3×). The Kaiser test was negative. Fmoc protecting group from the ε-amine group of lysine was removed by 20% piperidine in DMF (2×). Next, the resin was washed with DMF (3×), IPA (3×), DMF (3×). The Kaiser test was positive. In order to prepare the peptide resin to the final step of the synthesis it was washed with DCM (3×) and placed in a vacuum desiccator for 24 h. The peptide was cleaved from the resin with anisol:HF (1:9, v/v) in use of the standard protocol. The reaction was carried out for 3 h. The peptide was purified by preparative high performance liquid chromatography (HPLC) using the C-12 reverse phase column. Elution was achieved by linear gradient 0%-30% (A) was 0.05% TFA in water and buffer (B) was 0.05% TFA in ACN. The fractions were analyzed using an analytical RP-HPLC on C-12 column.

Rf=15, 97 (gradient 0-30% B in 30 minutes);

MS—[M+H]+ calc: 511.3, found. 511.3.

[M+2H]2+ calc: 256.2, found. 256.2.

EXAMPLE 2

Monomeric compound H-c[Lys-Pro-Glu]-Arg-OH was obtained according to the above scheme, but using Boc-Arg (Tos)-PAM resin in a loading 0.23 mmol/g.

Analytical Data:

Rf=15, 97, (gradient 0-30% B for 30 min)

MS—[M+H]+ calc: 511.3, found. 511.3.

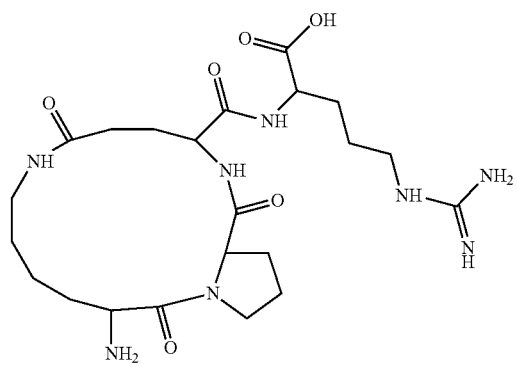 [SMILES: N=C(N)NCCCC(NC(=O)C1CCC(=O)NCCCCC(N)C(=O)N2CCCC2C(=O)N1)C(=O)O]

Selected compounds were tested in vitro by measuring the inhibition binding of VEGF165 to NRP-1. This assay allows the determination of percentage inhibition of the tested compound at a predetermined concentration.

Determination of the Inhibitory Activity of the Tested Compounds.

The evaluation of the inhibitory effect of peptidomimetics was performed using an enzymatic method denoting the spectrophotometric displacement of the $VEGF_{165}$ ligand from the specific receptor by the evaluated compound. The studies were performed using polystyrene 96-well plates (Maxisorb, Nunc.).

The Procedure for Determining the Inhibition of VEGF165/NRP-1.

To evaluate the biological inhibitory activity of selected molecules in each well of flat bottom polystyrene plate of 96-wells (Maxisorb, Nunc,) a 100 µl of a solution containing 2 µg/ml of anti-Fc IgG (Sigma-Aldrich) dissolved in a phosphate buffer PBS (PBS, Sigma) was placed. The plate was allowed to stand overnight at 4° C.

The next day, wells were washed three times with 100 µl PBS, and then saturated with 2% bovine serum albumin (BSA, Sigma) in PBS in order to eliminate non-specific interactions. After 2 hours of incubation at 37° C. the following solutions were added portionwise:

50 µl of purified recombinant rat NRP1-Fc (R&D Systems, Abingdon, UK) in a solution of 20 ng/well protein dissolved in PBS-BSA 0.1% tween-80 0.005% (PBT), 50 µl of compound solution in PBT in an appropriate concentration 50 µl of biotinylated VEGF165 in a concentration 1 nM (R&D Systems) dissolved in PBT containing 2 µg/ml heparin (Sigma). The total volume of added solution was 150 µl.

After an overnight incubation at 4° C., the wells were washed with PBT and treated with streptavidin-HRP polymer (horseradish peroxidase, Sigma). The plate was incubated for 1 hour at room temperature. Next, the wells were washed with 200 µl PBT and substrate ABTS (2,2'-azinobis [3-ethylbenzothiazoline-6-sulfonic acid]-diammonium salt) (Sigma) was added.

After 2 hours, the absorbance was measured at wavelength of 415 nm with respect to 470 nm.

To determine IC50 for the best compounds measurements were made at concentrations from 0.03 to 10 µM or 0.15 to 5 mM. In the control wells the tested compound was absent, but the respective concentration of DMSO was maintained. The heptapeptide A7R (ATWLPPR (SEQ ID NO:1)) was used as a positive control on every 96-well plate.

TABLE 1

The results of inhibition studies of the heptapeptide A7R.

| Code | Concentration | | | | |
|---|---|---|---|---|---|
| | 100 µM | 10 µM | 3 µM | 1 µM | 0.3 µM |
| A7R | 87.8% | 74.9% | 55.1% | 36.3% | 14.6 |

TABLE 2

Test results of inhibition of cyclic peptidomimetics of the invention.

| Exemplary cyclic peptidomimetics (dimers) | Concentration | | | |
|---|---|---|---|---|
| | 5 µM | 1.5 µM | 0.5 µM | 0.15 µM |
| (c[Lys-Pro-Glu]-Arg-OH)$_2$ | 81.2 | 72.6 | 58.4 | 43.9 |
| (H-c[Dap-Pro-Glu]-Arg-OH)$_2$ | 64.0 | 43.4 | 39.9 | 21.3 |
| c[Dap-Pro-Glu]-Arg-OH | 63.5 | 34.6 | 30.7 | 22.2 |
| (H-c[Lys-D-Pro-Glu]-Arg-OH)$_2$ | 69.8 | 51.8 | 48.5 | 29.9 |
| (c[Dab-Pro-Glu]-Arg-OH)$_2$ | 74.8 | 63.5 | 54.8 | 40.6 |
| (H-c[Dab-Pro-Glu]-Arg-OH)$_2$ | 72.1 | 64.3 | 46.8 | 40.7 |
| (c[Arg-Pro-Glu]-Arg-OH)$_2$ | 80.4 | 72.6 | 66.1 | 53.3 |
| (c[hArg-Pro-Glu]-Arg-OH)$_2$ | 80 | 63.7 | 40.7 | 31.7 |

| Exemplary cyclic peptidomimetics (monomers) | Concentration | | | |
|---|---|---|---|---|
| | 10 µM | 3 µM | 1 µM | 0.3 µM |
| H-c[Lys-Pro-Glu]-Arg-OH | 94.7 | 86.7 | 76.5 | 61.7 |
| H-c[D-Lys-Pro-Glu]-Arg-OH | 14.7 | 12.5 | 11.8 | NS |
| H-c[Lys-Pro-Asp]-Arg-OH | 46.6 | 35.4 | 27.8 | 14.6 |
| c[Orn-Pro-Glu]-Arg-OH | 23.1 | 5.1 | 0.3 | NS |

This test indicates potential antiangiogenic effects. The novel compounds of the invention are significantly better than standard peptide A7R, because they show inhibitory activity at nM concentrations.

In comparison to the heptapeptide A7R, which exhibits rapid loss of activity with decreasing concentrations (reduction of concentrations of 10-0.3 µM result in a 5-fold decrease in inhibition) in the case of the compounds of the invention at similar concentrations in the range 5-0.15 PM is only about 2-fold decrease in inhibition—only half (inhibition decreases from 70-80% to 41-55%).

For some compounds the IC$_{50}$ was determined:

(c[Lys-Pro-Glu]-Arg-OH)$_2$, IC$_{50}$=0.46 µM

H-c[Lys-Pro-Glu]-Arg-OH, IC$_{50}$=0.18 µM

The invention claimed is:

1. A cyclic peptidomimetic of general formula I:

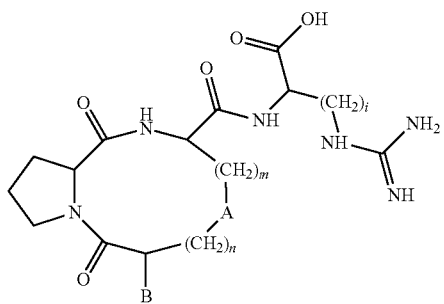

where m=from 0 to 4, n=from 0 to 4, i=3 or 4, and
where A is selected from the group:
—CO—NH—; —NH—CO—; —S—S—; —HN—CO—NH—, $CH_2$—$CH_2$—; —$CH_2$—NH—; —NH—$CH_2$—;

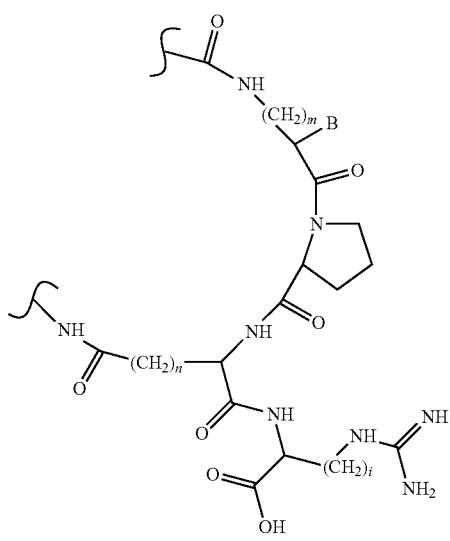

B is selected from the group:
—$(CH_2)_d$-$NH_2$, where d=from 0 to 4;

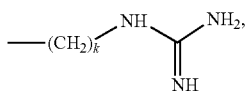

where k=3 or 4,
wherein, each chiral center may have L or D and/or R or S configuration,
and pharmaceutically acceptable salts, hydrates or other pharmaceutically acceptable complexes thereof.

2. The cyclic peptidomimetic of claim 1, which inhibits VEGF 165 and NRP-1.

3. The cyclic peptidomimetic of claim 1, which exhibits antiangiogenic properties.

4. The cyclic peptidomimetic of claim 1, which is a monomer with a general formula:

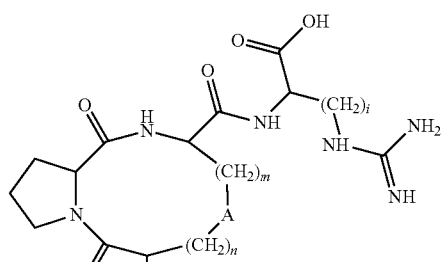

where m=from 0 to 4, n=from 0 to 4, i=3 or 4, and
where A is selected from the group: —CO—NH—; —NH—CO—; —S—S—; —HN—CO—NH—, $CH_2$—$CH_2$—; —$CH_2$—NH—; —NH—$CH_2$—, B is selected from the group:
—$(CH_2)d$-$NH_2$, where d=from 0 to 4;

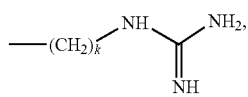

where k=3 or 4, wherein each chiral center may be L or D configuration or the R or S, and pharmaceutically acceptable salts, hydrates or other pharmaceutically acceptable complexes thereof.

5. The cyclic peptidomimetic of claim 1, which is a dimer of a general formula:

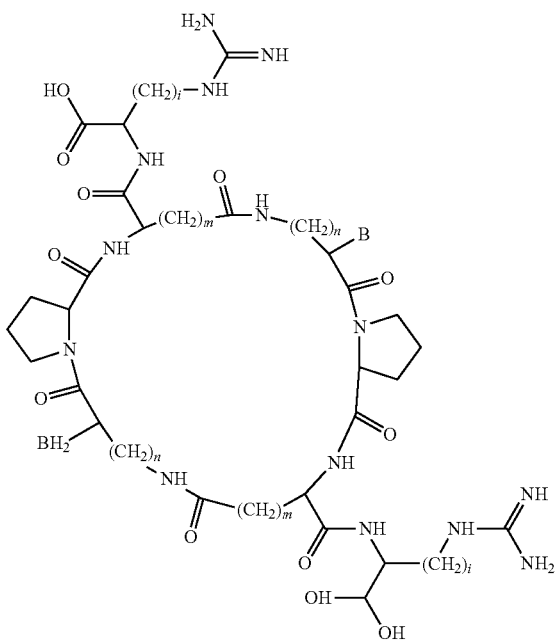

where m=from 0 to 4, n=from 0 to 4, i=3 or 4, and
B is selected from the group: —$(CH_2)_d$—$NH_2$, where d=from 0 to 4;

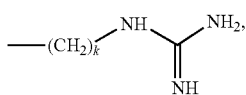

where k=3 or 4,
wherein each chiral center may be L or D configuration or the R or S, and pharmaceutically acceptable salts, hydrates or other pharmaceutically acceptable complexes thereof.

6. The cyclic peptidomimetic of claim 1, selected from the group consisting of the compounds of formulas:

(c[Lys-Pro-Glu]-Arg-OH)$_2$ (c[Dab-Pro-Glu]-Arg-OH)$_2$ (H-c[Dab-Pro-Glu]-Arg-OH)$_2$ (c[Arg-Pro-Glu]-Arg-OH)$_2$

H-c[Lys-Pro-Glu]-Arg-OH.

7. A pharmaceutical composition comprising, as an active ingredient, the cyclic peptidomimetic of claim 1 and a pharmaceutically acceptable carrier and/or a pharmaceutically acceptable additive.

8. The composition of claim 7, which is for the treatment of tumors and/or chronic inflammation, psoriasis, diabetes, degenerative diseases of the eye, nephropathy and neuropathy.

9. A method for treating tumors or a disease associated with angiogenesis by administering a medicament wherein the cyclic peptidomimetic of claim 1 is used as an active ingredient in the medicament.

10. The method of claim 9, wherein the disease associated with angiogenesis is selected from, chronic inflammation, psoriasis, diabetes, degenerative eye diseases, nephropathy and neuropathy.

11. The method of claim 10, wherein the chronic inflammation is rheumatoid arthritis or inflammatory bowel disease.

12. The method of claim 9, wherein the medicament is in a dosage form adapted for infusion or intravenous injections or implants.

13. The method of claim 10, wherein the neurodegenerative diseases of the eye is age-related macular degeneration (ARMD).

* * * * *

SEQUENCE LISTING

<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: synthetic

<400> SEQUENCE: 1

Ala Thr Trp Leu Pro Pro Arg
1               5